US010161885B2

(12) United States Patent
Barak et al.

(10) Patent No.: US 10,161,885 B2
(45) Date of Patent: Dec. 25, 2018

(54) OPTICAL PHASE MEASUREMENT METHOD AND SYSTEM

(71) Applicant: Nova Measuring Instruments Ltd., Rehovot (IL)

(72) Inventors: Gilad Barak, Rehovot (IL); Danny Grossman, Herzliya (IL); Dror Shafir, Kiryat Ono (IL); Yoav Berlatzky, Kibbutz Beit Guvrin (IL); Yanir Hainick, Tel-Aviv (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 15/300,768

(22) PCT Filed: Apr. 12, 2015

(86) PCT No.: PCT/IL2015/050389
§ 371 (c)(1),
(2) Date: Sep. 29, 2016

(87) PCT Pub. No.: WO2015/155779
PCT Pub. Date: Oct. 15, 2015

(65) Prior Publication Data
US 2017/0016835 A1  Jan. 19, 2017

Related U.S. Application Data

(60) Provisional application No. 61/975,989, filed on Apr. 7, 2014.

(51) Int. Cl.
*G01N 21/956* (2006.01)
*G01N 9/02* (2006.01)
(Continued)

(52) U.S. Cl.
CPC ....... *G01N 21/956* (2013.01); *G01B 9/02007* (2013.01); *G01B 9/0209* (2013.01);
(Continued)

(58) Field of Classification Search
CPC ............. G01N 21/956; G01N 21/8806; G01N 2021/8848; G01B 11/0675;
(Continued)

(56) References Cited

U.S. PATENT DOCUMENTS

| 6,611,336 B1 | 8/2003 | Walmsley et al. |
| 6,985,232 B2 * | 1/2006 | Sezginer ................. G01J 3/453 356/451 |

(Continued)

FOREIGN PATENT DOCUMENTS

| WO | 2011/104713 A1 | 9/2001 |
| WO | 2014/102792 A | 7/2014 |

OTHER PUBLICATIONS

Griffiths, P. and de Hasseth, J.A. Fourier Transform Infrared Spectrometry (2nd ed.). Wiley-Blackwell—pp. 2, 106-108 (May 18, 2007).
(Continued)

*Primary Examiner* — Dominic J Bologna
(74) *Attorney, Agent, or Firm* — Browdy and Neimark, PLLC

(57) ABSTRACT

A measurement system for use in measuring parameters of a patterned sample is presented. The system comprises: a broadband light source; an optical system configured as an interferometric system; a detection unit; and a control unit. The interferometric system defines illumination and detection channels having a sample arm and a reference arm comprising a reference reflector, and is configured for inducing an optical path difference between the sample and reference arms; the detection unit comprises a configured
(Continued)

and operable for detecting a combined light beam formed by a light beam reflected from said reflector and a light beam propagating from a sample's support, and generating measured data indicative of spectral interference pattern formed by at least two spectral interference signatures. The control unit is configured and operable for receiving the measured data and applying a model-based processing to the spectral interference pattern for determining one or more parameters of the pattern in the sample.

19 Claims, 13 Drawing Sheets

(51) Int. Cl.
  *G01B 11/06* (2006.01)
  *G01N 21/88* (2006.01)
  *G01B 9/02* (2006.01)

(52) U.S. Cl.
  CPC ..... *G01B 9/02032* (2013.01); *G01B 9/02072* (2013.04); *G01B 11/0675* (2013.01); *G01N 21/8806* (2013.01); *G01B 2210/56* (2013.01); *G01B 2290/70* (2013.01); *G01N 2021/8848* (2013.01)

(58) Field of Classification Search
  CPC .............. G01B 9/02032; G01B 9/0209; G01B 9/02007; G01B 9/02072; G01B 2290/70; G01B 2210/56
  See application file for complete search history.

(56) References Cited

U.S. PATENT DOCUMENTS

| | | | |
|---|---|---|---|
| 7,061,625 B1* | 6/2006 | Hwang | G01B 11/2441 356/497 |
| 2005/0254063 A1* | 11/2005 | Hill | G01N 21/956 356/512 |
| 2006/0158657 A1* | 7/2006 | De Lega | G01B 9/023 356/497 |
| 2007/0206201 A1 | 9/2007 | de Groot et al. | |
| 2008/0174784 A1* | 7/2008 | Colonna De Lega | G01B 9/02057 356/511 |
| 2008/0221837 A1* | 9/2008 | De Groot | G01B 11/2441 702/189 |
| 2009/0009773 A1 | 1/2009 | Sugiyama et al. | |
| 2012/0069326 A1* | 3/2012 | Colonna de Lega | G01B 11/0675 356/73 |
| 2015/0077760 A1* | 3/2015 | Koerner | G01B 9/02008 356/496 |

OTHER PUBLICATIONS

Rick Trebino, Frequency-Resolved Optical Gating: The Measurement of Ultrashort Laser Pulses. Springer, pp. 101-115 (2002).
Mitsuo Takeda et al. "Fourier-transform method of fringe-pattern analysis for computer-based topography and interferometry". J. Opt. Soc. Am. 72 156 (1982)—Abstract attached.

* cited by examiner

Tilted Field

$$\Delta z = x \tan \theta$$

Defocused Field

$s = \sin \theta$
dimensionless pupil coordinate $$\Delta z = h \cos \theta = h\sqrt{1 - s^2}$$

Tilted Pupil/Displaced

$$\Delta z = s \Delta x$$

Tilted Pupil/Displaced

$$\Delta z = s \Delta x$$

(GENERAL ART)

OPTICAL PHASE MEASUREMENT METHOD AND SYSTEM

TECHNOLOGICAL FIELD

The present invention is generally in the field of optical measurement techniques, and relates to an optical system and method for determining parameters and/or properties of a patterned sample utilizing phase measurements, particularly useful in semiconductor industry.

BACKGROUND

The constant progress in semiconductor technology demands for the fabrication of ever smaller devices. This development has to be accompanied by concurrent improvement in metrology capabilities, in order to monitor and control the fabrication process.

Over the last few decades, optical critical dimension (OCD) metrology has taken a pivotal role in semiconductor manufacturing process, due to its extreme sensitivity, accuracy, flexibility and speed. In order to provide adequate improvement of the metrology capabilities, OCD tools have gone through extensive improvement and refinement, and can provide today extremely accurate broadband spectral measurements and extremely high throughput.

In addition to the process of improving the basic tool characteristics, another venue by which OCD performance can be improved is through diversifying the measured information. Commonly measured optical properties are the reflectivity for different incidence angles, azimuths, polarizations and wavelengths. In addition, the relative phase between reflected TE and TM polarization components can be accessed through (e.g.) ellipsometric measurements.

Another important attribute of light scattered from a patterned structure is its spectral phase. This quantity describes the relative phase between the incident and reflected electromagnetic waves. Typically, this phase has different values for different wavelengths, incident angles\azimuths and polarizations.

Since accessing the phase directly is not possible at optical frequencies, one has to use interference effects, usually observed with an interferometer, and recover the encoded phase information from the interference effects. Most interferometers consist of a split optical path that is recombined to form interference fringes. One arm of the path is kept as a reference, and the other interacts with the sample. The interference signal from these two components is then used to extract the spectral phase.

U.S. Pat. No. 6,985,232 describes a phase-sensitive interferometeric broadband reflectometer for optically inspecting and evaluating a subject. According to this technique, a broadband optical beam is split into probe beam and reference beam portions; the probe beam is directed to be reflected by the subject; after the probe beam has been reflected by the subject, the probe beam and the reference beam are rejoined. The length of the path traveled by the probe beam or the reference beam is modulating within a predetermined range during the measurements. Then, spectroscopic analysis of the rejoined beams is performed on a per-wavelength basis at a selected set of points within the predetermined range.

GENERAL DESCRIPTION

There is a need in the art for a novel phase measurement technique, which allows effective measurement with desirably high signal-to-noise ratio in the measured signal. Also, it might be desired to have a measurement system eliminating or at least significantly reducing a requirement to movement of the elements of an optical system.

The present invention provides a novel system and method for spectral phase measurements, by providing a spectral interferometric system, where a spectral interference pattern is detected by a spectral sensor and is in the form of multiple (at least two) spectral interference signatures corresponding to different (at least two) optical path differences (OPDs) between the sample and reference arms. In some embodiments, such spectral interferometric system utilizes a cross-polarization based measurements, by using polarization filtering in the illumination and detection channels. In some embodiments of the invention, spectral interference pattern (multiple spectral signatures) is obtained using a single exposure (single measurement) at arbitrary z-position, i.e. arbitrary distance between the optical paths of a reference light beam and a probe light beam interacting with the sample. In this connection, the following should be understood:

As indicated above, spectral phase can be measured using interferometric measurements. Traditional interferometry techniques require tight control of a path length difference in order to achieve accurate measurement results. In homodyne interferometers (such as phase shift interferometry), full retrieval of phase information requires a succession of measurements (at least 3 successive measurements), using several path length phase shifts. This usually requires a sequential measurement process, and measurement accuracy is compromised by setup instability during the sequence. These challenges also carry over to white-light interferometers. Also, commonly used techniques based on a swept source, vertical/phase scanning, and multi-z technique, typically use a sequential measurement process:

Achieving adequate system stability in a wafer metrology tool is an even greater challenge due to the following additional factors. Usually, such systems require high speed motion for sampling wafers at multiple points with high throughput. This adds heavy, high-precision machinery operating at high accelerations and velocities to the system with their associated problems, such as vibrations, settling times, air-flow and turbulence, and heating and cooling cycles. In addition, wafers are relatively large samples, complicating matters even further due to the large frame that has to straddle the wafer. This exposes the system to higher sensitivity to short-term effects, such as vibrations and turbulence, as well as long-term effects such as thermal expansion and chuck contamination. Finally, the wafer stack diversity and variability introduces shifts in absolute height (z) measurement from the wafer (for both optical and capacitive sensors), adding undesirable complexity to the system.

In view of the above, it might be desirable to have an interferometer that allows full spectral phase retrieval using a single exposure at arbitrary Z values.

The present invention deals with several of the main difficulties of using broadband ('white light') and/or phase-shift interferometry for measuring the spectral phase, in order to perform OCD and thin film metrology, as well as material optical properties investigation.

The present invention provides effective calibration schemes and data analysis methods. As will be described more specifically further below, specific calibrations can be used to account for dominant system-related effects on the measured signal. For spectral phase measurements, there is a freedom in choosing what measured property to use in order to extract the required data. The inventors have shown that by correct choice of the quantity to be compared with the calculations, it is possible to significantly improve sensitivity, and obtain a robust measurement.

The present invention also provides algorithmic approaches to account for system-related effects in the analysis of spectral reflectometry data. For example, the inventors have shown how vibrational sensitivity, which is one of the main factors limiting usability of interferometric methods, can be accounted for using correct algorithmic treatment.

As indicated above, the present invention provides for constructing a unique implementation of spectral phase measurement, based on white-light interferometer that allows obtaining the full spectral phase, using cross-polarization scheme and/or a single exposure at arbitrary z (dimension along the optical axis). The single exposure renders the system immune to transient instability effects that compromise sequential measurements. As is common in most white-light interferometers, the height ambiguity of a single measurement can be compensated for by performing a mathematical transformation on the measured data (such as unwrapping), and/or by prior-knowledge of estimated value of the height. Since in the field of OCD the structure under examination is usually known up to some variability in its dimensions, this prior knowledge is mostly available. The invention provides several methods to achieve single-exposure phase measurement (which can be expanded with additional measurements as required). These methods include spectrographic white-light interferometry; spectral heterodyne white-light interferometry; position-dependent spectral white light interferometry.

The invention also provides a method for spectral phase measurement based on several interferometric measurements. In this case, specially designed algorithms are used to extract an accurate phase by taking into account several data sets and efficiently canceling noise effects. These measurements can be taken at different optical path differences (OPD's) or during a z scan.

The invention includes a measurement scheme enabling an interferometric measurement at many OPDs simultaneously and by that achieving better noise cancelation.

In addition to the measurement methods, the invention provides several algorithmic methods enabling accurate and robust analysis of the measured data. These methods can be specifically tailored to the challenges imposed by the interferometric measurements.

The processing of the measured data includes fitting procedure between the measured data and a theoretical model. Typically, the fitting process includes merit function definition. The merit function is a measure of the degree of fit between calculated (theoretical) and measured data. The merit function may be the RMS error between measurement and calculation data pieces, where each of the measurement and calculation data pieces is in the form of reflected intensity I and phase $\phi$ simultaneously. For example, each of the reflected intensity and phase may be a function of the wavelength(s) used in the measurements, polarizations and incident\reflected angles. Other types of data can be presented and interpreted e.g. complex electric field components or sin/cos of the measured phase.

As interferometry provides the most straightforward method for phase measurement, one of the methods of the invention described below involves using time-dependent measurements for this purpose. This approach bypasses many of the difficulties introduced by interferometric measurements.

The invention thus provides spectral phase measurement for OCD applications. The technique of the invention can be specifically used for CD measurements, as compared to the traditional interferometry which is typically used only for thickness and z related measurements. The present invention utilizes the spectral nature of the phase extraction or a so-called "interferometric spectrum". The technique of the invention provides a model based solution for spectral phase measurements, as well as polarized spectral phase measurements, and allows for combining spectral phase measurements with regular Spectral Reflectometry (SR). The measurement technique of the invention can advantageously be incorporated in automatic optical inspection (AOI) system, utilizing normal and/or oblique incidence mode.

Thus, according to one broad aspect of the invention, there is provided a measurement system for use in measuring parameters of a patterned sample, the system comprising: a broadband light source; an optical system configured as an interferometric system; a detection unit; and a control unit; wherein the interferometric system defines illumination and detection channels having a sample arm and a reference arm comprising a reference reflector, and is configured for inducing an optical path difference between the sample and reference arms; the detection unit comprises a configured and operable for detecting a combined light beam formed by a light beam reflected from said reflector and a light beam propagating from a sample's support, and generating measured data indicative of spectral interference pattern formed by at least two spectral interference signatures; and said control unit is configured and operable for receiving the measured data and applying a model-based processing to the spectral interference pattern for determining one or more parameters of the pattern in the sample.

In some embodiments, the interferometric system comprises polarizers in the illumination and detection channels.

The interferometric system comprises a mechanism for inducing the optical path difference (OPD) between the sample and reference arms. In some embodiments, such OPD inducing mechanism comprising a driving unit for controllably moving either one or both of the reflector and the sample's support along an optical axis of the interferometric system, while both the reflector and sample are oriented perpendicular to the optical axis.

In some other embodiments, such OPD mechanism is implemented without a need for moving the reflector and/or sample. This can be achieved by orienting at least one of the sample's support and the reflector with a fixed tilted position with respect to the optical axis of the interferometric system. In another example, the OPD mechanism is implemented by inducing defocusing effect on illuminating light beam propagating along the reference arms towards the reflector, e.g. by locating the reflector in a plane parallel to and spaced-apart from a focal plane of an objective lens unit of the interferometric system. Yet another example for implementing the OPD mechanism without any moving element is by configuring the reflector as a retro-reflector assembly.

In some embodiments, the light source is configured and operable for producing illumination in the form of ultra short pulses.

According to another broad aspect of the invention, there is provided an optical system for use in measuring parameters of a patterned sample, the optical system being configured as a spectral interferometric system defining illumination and detection channels having a sample arm and a reference arm comprising a reference reflector, and being configured for inducing an optical path difference between the sample and reference arms, such that combined light beam, propagating along the detection channel to a spectrometer, is formed by a light beam reflected from said reflector and a light beam propagating from a sample and is indicative of spectral interference pattern formed by at least two spectral interference signatures corresponding to at least two optical path differences.

According to yet another broad aspect of the invention, it provides a method for use in measuring parameters of a patterned sample, the method comprising:

directing broadband light through an interferometric optical system having a sample arm and a reference arm with an optical path difference between the sample and reference arms;

detecting a combined light beam formed by a light beam reflected from a reflector in the reference arms and a light beam propagating from the sample under measurements, and generating measured data indicative of spectral interference pattern formed by at least two spectral interference signatures; and applying a model-based processing to the spectral interference pattern and determining one or more parameters of the pattern in the sample.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which.

DETAILED DESCRIPTION OF EMBODIMENTS

Figure 1A:
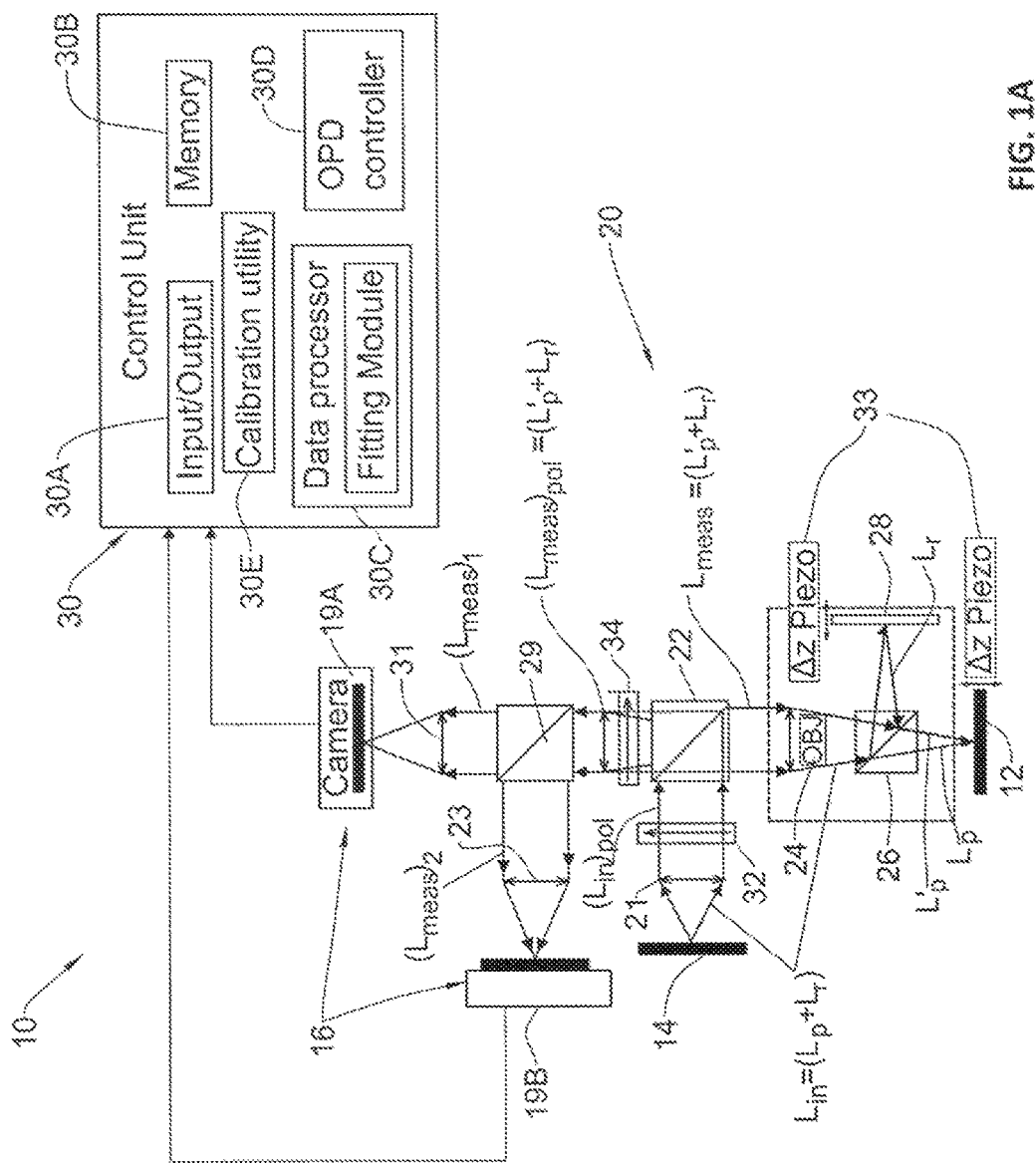
FIG. 1A schematically illustrates a measurement system of the invention configured as a spectral interferometer system.

Reference is made to FIG. 1A schematically illustrating an example of a measurement system of the invention, which is configured as a spectral interferometer system operable to measure spectral phase of light returned (reflected and/or scattered) from a patterned structure (e.g. semiconductor wafer) to enable determination of the parameters of the pattern.

It should be noted that in this specific but not limiting example of FIG. 1A, as well as examples of FIGS. 1B and 1C described below, the system is exemplified as being configured for operation with the normal incidence mode and bright field measurement mode. It should, however, be understood that the invention is not limited to this configuration, and generally, measurement can be obtained in any (oblique or other) angle-of-incidence mode, as well as can utilize dark-field measurement mode or a combination of bright- and dark-field measurement modes. Moreover, as will be described below with reference to FIG. 1A, the system may implement polarization-based dark-field measurement mode while having a principle normal-incidence bright-field configuration.

The measurement system is based on a general spectral reflectometer configuration, where sample reflectivity is accurately measured, but being modified to utilize the interferometric measurements according to the invention. More specifically, the measurement system, generally designated 10 in FIG. 1A, includes a light source 14 providing broadband input light $L_{in}$ (white light) including probe and reference light beams $L_p$ and $L_r$ accordingly, a detection unit 16; and an optical system 20 configured as light directing arrangement for directing light from the light source 14 towards a sample/structure under measurements located on a sample's support 12 and a towards an optical path difference inducing mechanism 28 (planar mirror in this example) and directing returned light to the detection unit 16.

In the example of FIG. 1A, such a planar mirror is located in a plane perpendicular to the optical axis of the optical system 20 (i.e. "untilted mirror"), and may or may not be movable along the optical axis. Also, in the example, of FIG. 1A, the detection unit 16 includes spectrometer (spectrophotometer) 19B for generating spectral data of light incident thereon, and also optionally includes an imaging detector 19A for navigating to measurement sites on the structure. Output of the detection unit 16 is communicated (via wires or wireless signal communication) to a control unit 30.

The optical system 20 is configured for defining an illumination channel for propagating input light $L_{in}$ from the light source 14 towards the structure plane 12, and a detection channel for propagating light being measured $L_{meas}$ to the detection unit 16. The input light $L_{in}$ is to be split into probe and reference beams $L_p$ and $L_{ref}$, and light being measured $L_{meas}$ includes reflection (scattering) $L'_p$ of the probe beam $L_p$ from an illumination region on the structure 12 and light $L_r$ reflected from a reference mirror 28.

The optical system 20 includes a beam splitter/combiner 22 which is configured for spatially separating between input light $L_{in}$ and light being measured $L_{meas}$, and an objective lens unit 24 (one or more lenses). In the present example of system configuration, which uses normal incidence and bright-field detection modes, these units 22 and 24 are located in both the illumination and detection channels. The light directing arrangement 20 also optionally includes a collimating lens 21 in the illumination channel, being in the optical path of input light $L_{in}$ propagating from the light source towards the beam splitter 22, and a tube lens 23 in the detection channel, being in the optical path of measured light propagating to the detection unit.

The optical system 20 further includes a beam splitter/combiner 26 which splits the input light $L_{in}$ into the probe and reference beams $L_p$ and $L_r$ and directs them respectively along the sample arm towards the structure 12 and along a reference arm towards the reference mirror 28. Mirror 28 reflects the reference beam $L_r$ back to the beam splitter/combiner 26 where it is combined with reflection (scattering) $L'_p$ of the probe beam $L_p$ from an illumination region on the structure 12 into a combined light beam $L_{meas}$ to be measured/detected. The combined light beam propagates to the detection unit 16, i.e. passes through the objective 24 and beams splitter 22 and further via the tube lens 23 which focuses it onto the spectrometer 19B of detection unit 16.

According to the invention, in this example of FIG. 1A, the optical system 20 includes polarizers 32 and 34 located in respectively, illumination and detection channels. More specifically, input light $L_{in}$ on its way from the light source 14 passes through the polarizer 32 and a specifically polarized (e.g. linearly polarized) input light $(L_{in})_{pol}$ is directed by beam splitter/combiner 26 to objective 24 which directs it to beam splitter/combiner 26. The latter splits polarized input light $(L_{in})_{pol}$ into probe and reference polarized beams $L_p$ and $L_r$ and directs them to respectively the structure on support 12 and reference mirror 28. Reflections from the structure and mirror $L'_p$ and $L_r$ are combined by beam splitter/combiner 26 into a combined light beam $L_{meas}$ having said specific polarization, which passes through the objective 24 and beam splitter 22 to the polarizer 34, which allows only light of said specific polarization $(L_{meas})_{pol}$ to propagate to the detection unit. This combined polarized light beam is divided by beam splitter 29 into light portions $(L_{meas})_1$ and $(L_{meas})_2$ which are directed to respectively the imaging detector 19A and spectral sensor (spectrometer) 19B. The spectrometer 19B measures every wavelength's intensity separately and accordingly measured data generated by the spectrometer corresponds to the spectral interference pattern. The system 10 also includes a driving unit 33 associated with either one or both of the mirror 28 and the sample's support 12 for controllably moving it/them along the optical axis, i.e. z-axis, thereby inducing optical path difference resulting in time variation of the spectral interference pattern. It should be understood that using polarizers 32 and 34 accommodated and oriented as described above actually provides a cross-polarization scheme, which results in the dark-field measurement mode. It should be understood, that when the mirror 28 is not used (i.e. is moved out of the optical path of incident light or is inactivated by the use of an appropriate shutter), the system 10 can operates as a spectral reflectometer. Accordingly, the same system 10 may be shifted between two different operational modes, as a spectral interferometer and spectral reflectometer.

Control unit 30 is typically a computer system including inter alia such utilities (software/hardware) as data input and output utilities 30A, memory 30B, data processor 30C, and an optical path difference controller 30D. Also optionally provided in the control unit is a calibration utility 30E, as will be described further below.

Figure 1B:
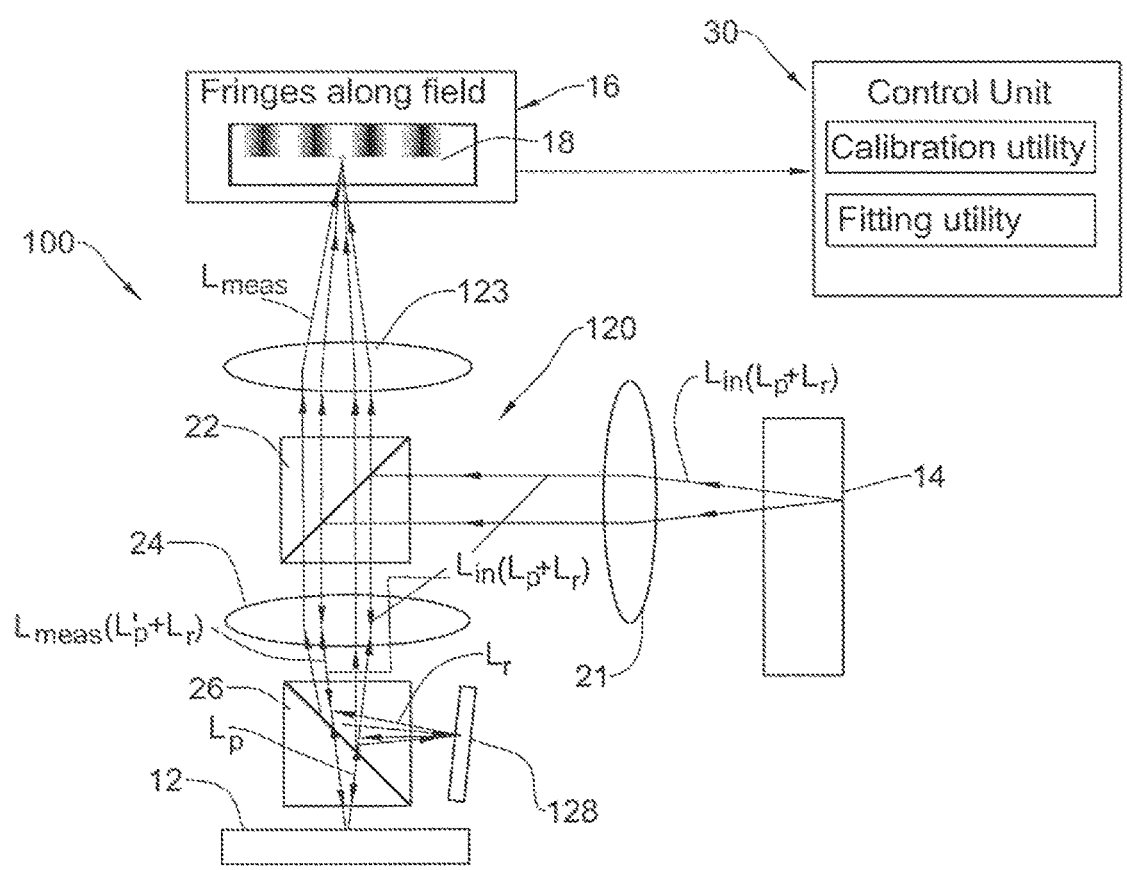
FIGS. 1B and 1C schematically illustrate two more examples of the measurement system of the invention utilizing tilted field (tilted mirror or sample)
Figure 1C:
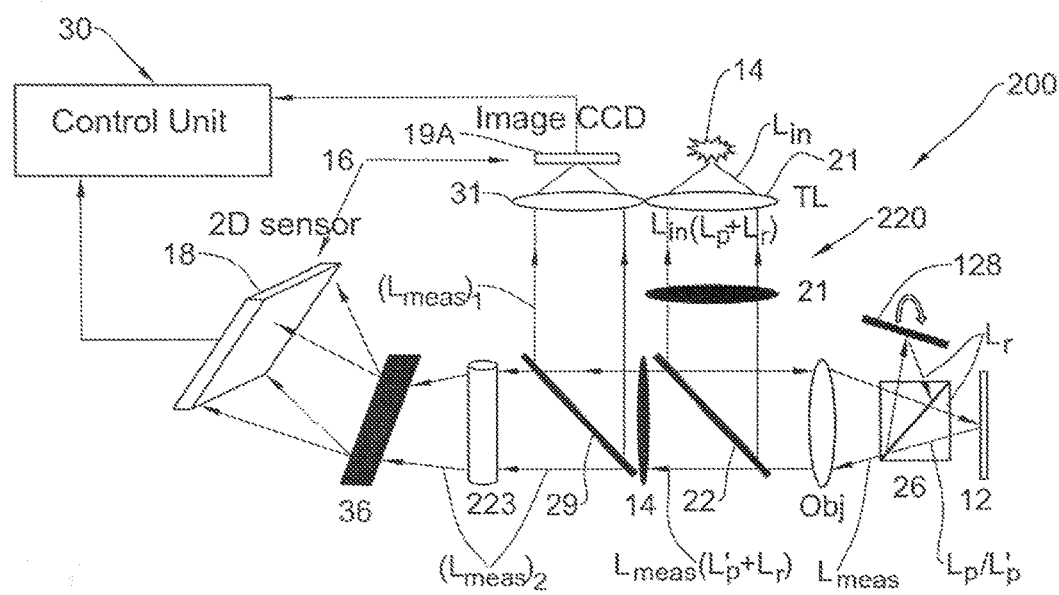
Figure 1D:
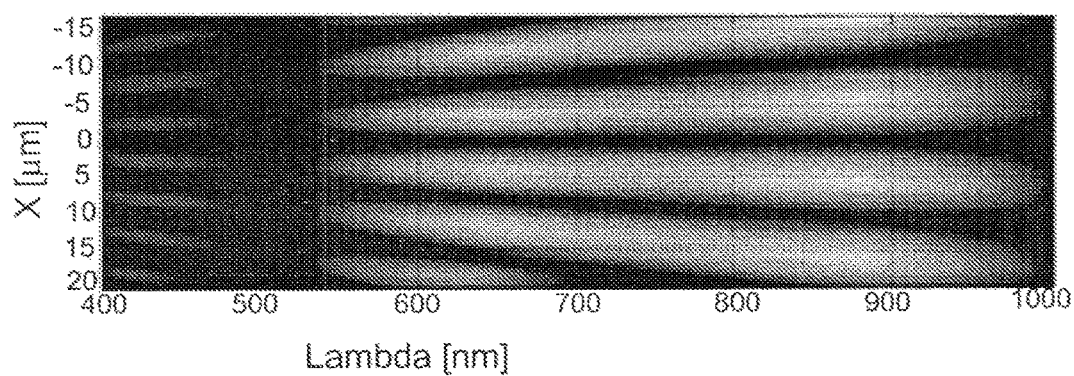
FIG. 1D illustrates interference pattern detected by the 2D sensor.

Reference is now made to FIGS. 1B-1D showing some other examples of the spectral interferometer system of the invention. To facilitate understanding, the same reference numbers are used for identifying components that are common in all the examples. In these non limiting examples, the spectral interferometric system utilizes a different principle for inducing optical path difference, while utilizing stationary mounted components of the system, i.e. mirror and/or sample' support are maintained at fixed positions, but is/are tilted with respect to the optical axis (tilted field). It should be noted that this tilted field approach can be combined with the above described polarization-based configuration of the illumination and detection channels.

Thus, a system 100 of the example of FIG. 1B is configured generally similar to that of FIG. 1A, but the optical system 120 in system 100 is different from optical system 20 of system 10 in that untilted movable or stationary mirror 28 used in optical system 20 is replaced in optical system 120 by a tilted mirror 128. Also, in figure FIG. 1B an imaging sensor (19A in FIG. 1A) is not shown, and accordingly beam splitter (29 in FIG. 1A) is also not shown. As indicated above, although polarizers are not shown in FIG. 1B, they may be used in system 100. System 200 shown in FIG. 1C is configured generally similar to system 10 of FIG. 1A in that it includes two detection channels defined by the imaging and spectral sensors, and optical system 220 (light directing arrangement) includes the beam splitter 29. However, this system 200, similarly to that of FIG. 1B, has tilted mirror 128. In the example of FIG. 1C, polarizers (not shown) may or may not be used.

Further, in system 100 (FIG. 1B) and system 200 (FIG. 1C), the detection unit 16 includes a 2D spectrometer 18. Accordingly, the optical systems 120 and 220, in examples of FIGS. 1B and 1C respectively, include cylindrical tube lenses 123 and 223 and diffraction gratings in the spectrometer detection channel, as specifically illustrated in FIG. 1C while not being shown in FIG. 1B.

Thus, according to some embodiments of the invention, exemplified in FIGS. 1B and 1C, the optical path difference (OPD) between the optical paths of the probe and reference beams $L_p$ and $L_r$ is created without movement of any optical element. This is achieved by providing one of the following stationary mounted arrangement: (1) tilted mirror or tilted sample's support; (2) inducing defocusing effect on the reference beam, e.g. by positioning the untilted mirror n a plane spaced-apart from a focal plane (plane conjugate to the focal plane of the objective); or (3) inducing a field shift to the reference beam, i.e. tilted pupil/displaced field, by configuring the mirror as a retro-reflector assembly (flips).

In the examples of FIGS. 1B and 1C, the tilted planar mirror embodiment is illustrated. This and other options will be described in more details further below.

Thus, input light $L_{in}$ from the light source 14 is split between the sample arm and the reference arm where the tilted mirror 128 is located. Light $L_r$ reflected from the reference mirror 128 is combined with light reflection $L'_p$ from the sample in the beam combiner 26 and directed to the detection unit. As more specifically shown in FIG. 1C, the spectral sensor 18 is a 2D sensor, and portion $(L_{meas})_2$ of the combined light beam $L_{meas}$ that is directed to the spectral sensor, preferably propagates through the cylindrical tube lens 223 and diffraction grating 36. Signals corresponding to different OPDs, due to tilt of the stationary reference mirror 128 are detected by the 2D sensor along one axis, whereas the other axis is a spectral signal representation. Since the mirror 128 is tilted and the sample is not tilted, every interference line occurs at different OPD similar to interference with additional z scan. It should be understood that the same would be obtained if the planar mirror is not tilted (i.e. is perpendicular to the optical axis) while the structure is located on a tilted support, i.e. OPD is induced in reference path or measurement one by tilt of mirror or sample. An interference pattern is presented in FIG. 1D.

It should be noted that the mirror tilt is calibrated in advance, and accordingly the spatial axis on the spectrograph is fully calibrated and every line represents a known OPD. It should also be noted that interferometric measurements are highly sensitive to vibrations, and interferometer systems that utilize multiple z measurements suffer from drifts and vibration changes between consecutive measurements. Using the principles of the above described embodiments of the invention (i.e. obtaining z-scan without moving the mirror in the reference arm), provides a more stable spectrograph scheme, since all z measurements are taken at the same time (single image) thus share drifts and vibrations.

Reference is made to FIGS. 2A-2D and FIGS. 3A-3C illustrating the principles of the three different implementations of the optical path difference (OPD) control between the optical paths of the probe and reference beams.

Figure 2A:
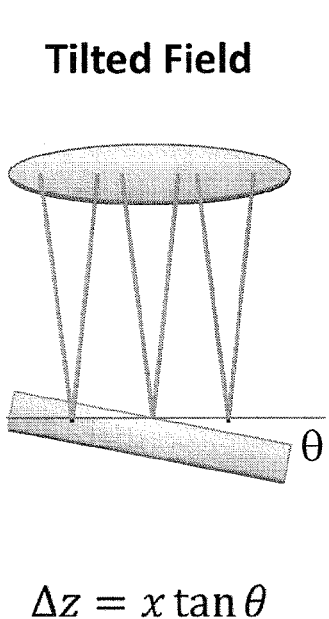
FIGS. 2A to 2D and 3A to 3C illustrate the principles of different implementations of the optical path difference (OPD) control between the optical paths of the probe and reference beams, where FIGS. 2A and 3A exemplify the configuration and spectrogram for tilted field embodiment utilizing tilting of the reference mirror or the sample, FIGS. 2B and 3B exemplify the configuration and spectrogram for defocused reference beam embodiment, and FIGS. 2C-2D and 3C exemplify the configuration and spectrogram for the use of retro-reflector.

As shown in the example of FIG. 2A, tilting the reference mirror or the sample (or, generally, tilted field) creates the OPD (along the Z-axis, or optical axis of the system) determined as:

$$\Delta z = x \cdot \tan \theta$$

wherein $\theta$ is the tilt angle, and x is the corresponding dimension in the sample plane.

Turning back FIGS. 1B and 1C, this configuration provides fringes linear in field, where $$a \tan(l/FOV) \cdot \theta = 1 \text{ Fringe}$$

Figure 3A:
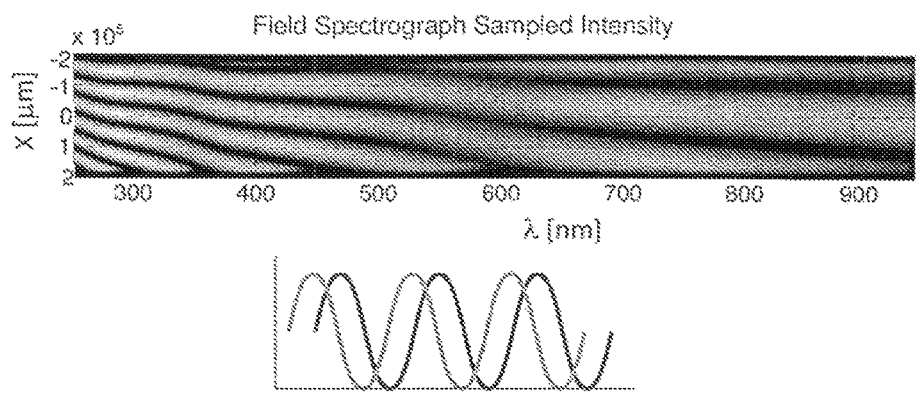

FIG. 3A shows the measured spectrogram (top) and the effect of phase in the shifts of cross fringes (bottom) for the Tilted Field Shear configuration of FIG. 2A.

Figure 2B:
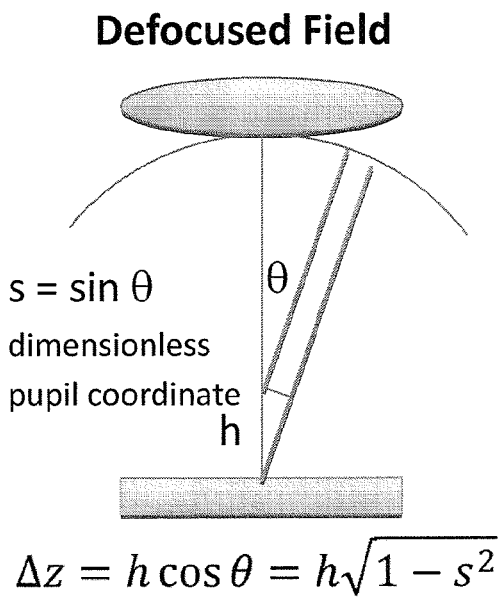

In the example of FIG. 2B, where defocused reference beam is used, the OPD is determined as:

$$\Delta z = h \cdot \cos \theta = h \cdot (1-S^2)^{1/2}$$

wherein $S = \sin \theta$, and h is the defocus.

Figure 3B:
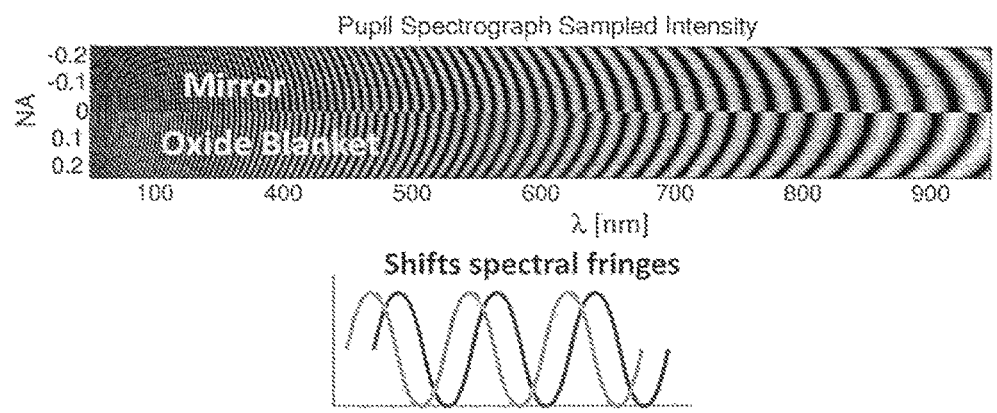

FIG. 3B shows the measured spectrogram (top) and the effect of phase in shifts of spectral fringes (bottom) for the Defocus Pupil Shear configuration of FIG. 2B.

Figure 2C:
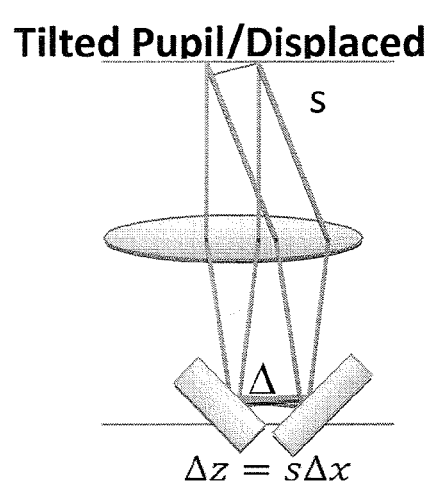
Figure 2D:
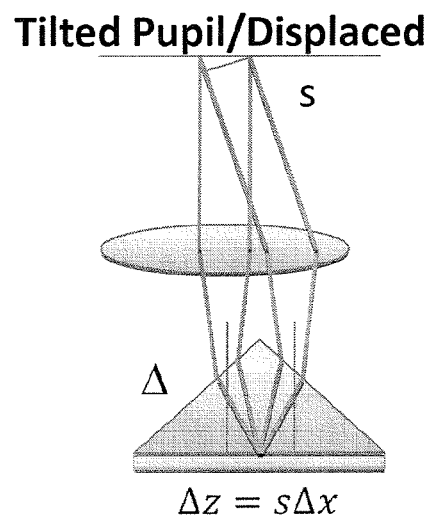

The configurations of FIGS. 2C and 2D provide that S is uniform in pupil, and linear fringes along pupil are obtained:

$$l/2NA \cdot Shift = 1 \text{ Fringe}$$

NA being a numerical aperture, and the OPD is determined as:

$$\Delta z = S \cdot \Delta x,$$

where $\Delta x$ is the defocus.

Figure 3C:
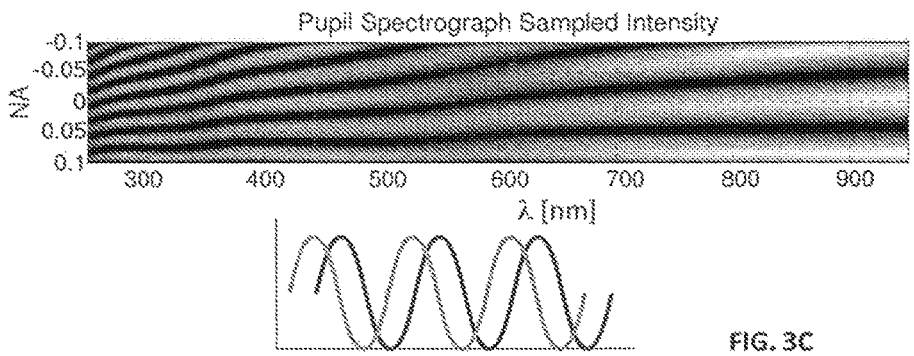

FIG. 3C shows the measured spectrogram (top) and the effect of phase in shifts of cross fringes (bottom) for the Tilted Pupil Shear configuration of FIGS. 2C and 2D.

As can be seen, the field shear configuration (FIG. 2A) seems to be the simplest option. Defocus shear configuration (FIG. 2B) can operate with smaller $\Delta z$ (less spectral fringes) if high NA objective is used. In the pupil shear configuration (FIGS. 2C and 2D), any deviation from ideal fringe form (linear or Fresnel) can be used to estimate the phase variation in NA.

Generally, the signal measured with the spectral interferometer is given by $$|I_k(p,z)|^2 = F_\Omega\{|S_k(p,\Omega) + R_k(\Omega) \cdot \exp(ikz)|^2\} \quad (1),$$

where $S_k(p)$ is the complex electric field reflected from the sample, $R_k$ is the electric field reflected from the reference mirror, and k is the wave vector. The fields are functions of the wave vector (magnitude and direction) and of the sample's parameters p (such as structure, thickness, optical properties etc.). The symbol $\Omega$ constitutes various system parameters, such as the optical numerical aperture, polarization, vibrations, optical aberrations etc. The function $F_{106}$ denotes the mathematical operation for summing over the various system parameters $\Omega$.

As seen in equation (1), the interferometric signal $|I_k(p,z)|$ depends not only on the sample parameters p but rather on the optical distance, z, between the sample and the reference mirror.

Figure 4:
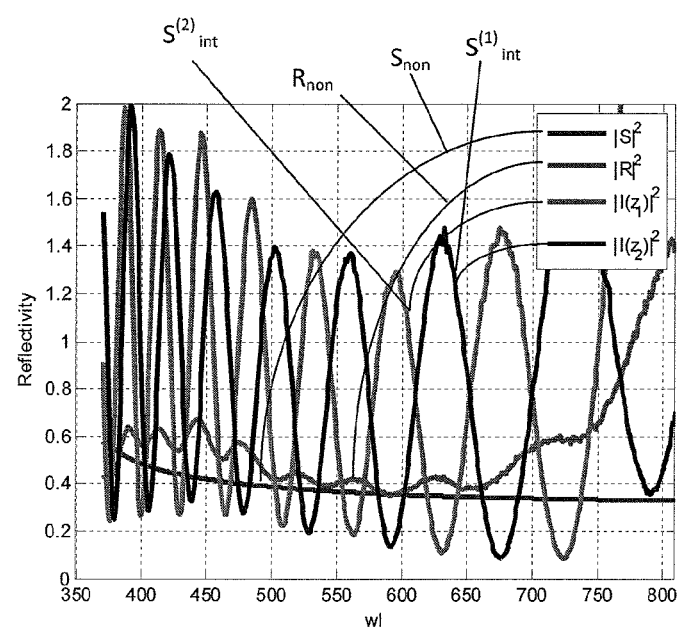
FIG. 4 illustrates interferometric and non-interferometric spectra.

FIG. 4 exemplifies interferometric and non-interferometric spectra. The interferometric spectra, $S^{(1)}_{int}$ and $S^{(2)}_{int}$ are measured using the interferometric spectrometer setup for respectively different sample positions $z_1$ and $z_2$ along the optical axis, and the non-interferometric spectra $S^{(1)}_{int}$ and $S^{(2)}_{int}$ are measured for respectively the sample and the reference, while blocking one of the interferometer arms. As can be seen in the graphs, when positioning the sample at different locations ($z_1$, $z_2$) with respect to the reference mirror, the signal changes significantly.

The reference reflectance $R_k$ is complex, and can be rewritten as $$R_k = |R_k| \cdot \exp(i\varphi_k),$$

where $\varphi_k$ is referred to as the "calibration phase".

Figure 5A:
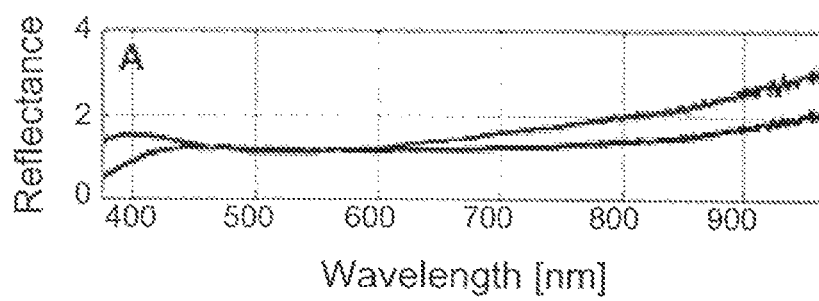
FIGS. 5A to 5C show the phase calibration of measured data for interferometric spectra at two z positions (FIG. 5A), difference between the fitted and measured spectra (FIG. 5B), and optimized phase function characterizing the optical system (FIG. 5C)
Figure 5B:
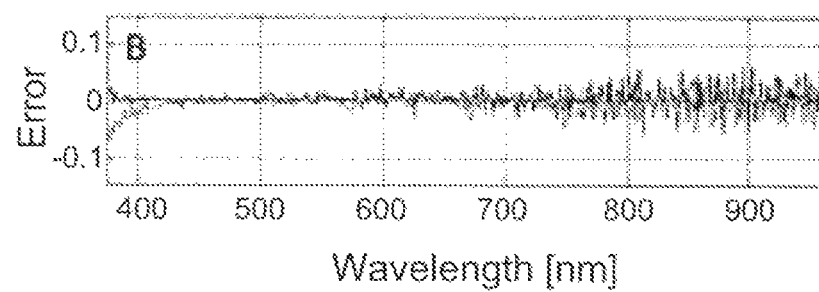
Figure 5C:
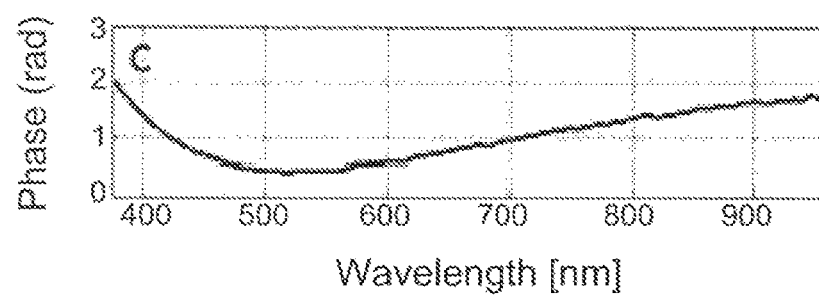

In order to correctly analyze the signal reflected from a measured target, it is first essential to accurately characterize the amplitude and phase of the reference mirror. The amplitude $|R_k|$ can be found for example by simply removing the sample from the system, thus equation (1) reduces to the square of the mirror amplitude reflectance (curve $R_{non}$ in FIG. 4). The calibration phase, however, is hidden in such a measurement. The phase calibration may be performed by placing a well characterized sample in the system (such as bare Silicon) and measuring the interference signal. In this connection reference is made to FIG. 5A-5C, showing the phase calibration of measured data for interferometric spectra at two z positions (FIG. 5A), difference between the fitted and measured spectra (FIG. 5B), and optimized phase function characterizing the optical system (FIG. 5C).

More generally, it is possible to control properties of the reference mirror, so as to optimize the metrology performance. As will be described below, the interference signal sensitivity depends on the relative phase between the sample and the reference mirror, as well as on their relative amplitudes. It is possible to change the mirror material\structure for optimal performance, and/or to obtain several measurements, with the mirror reflectivity being appropriately changed (e.g. using a mirror with printed pattern, and rotating it so as to change its reflectivity).

In order to extract the calibration phase from such measurements, the inventors considered the difference between the measured spectra and calculated spectra (theoretical, model-based data) as follows:

$$M_k(\varphi_k,z) = F_\Omega\{|S_k(\Omega) + |R_k(\Omega)| \cdot \exp(i\varphi_k) \cdot \exp(ikz)|^2\} - |I(z)|^2 \quad (2)$$

where $|I(z)|^2$ are measured spectra, and the term $$F_\Omega\{|S_k(\Omega)+|R_k(\Omega)|\cdot\exp(i\varphi_k)\cdot\exp(ikz)|^2\}$$

of the equation is calculated according to the known reflectance of the sample, reference mirror, and the integration operator. An optimization algorithm can be used to find the phase function $\varphi_k$ and z positions such that $|M_k(\varphi_k,z)|$ is minimized It is possible to use a single measurement at one z position, or various positions for noise reduction or better optimization.

This approach can be extended to several calibration targets for better calibration and optimization. Such approach can be especially important in order to allow accurate calibration for the full spectral range.

FIG. 5B shows the error spectrum $M_k(\varphi_k,z)$ for the optimizing function $\varphi_k$ which is shown in FIG. 5C. Indeed, once this function is assumed to characterize the phase induced by the optical system, the residual error is negligible.

It is important to note that in the calibration step it is possible to insert more fitting parameters to the optimization on $M_k$ such that various system parameters are introduced to the integration operator $F_\Omega\{\}$. These can include the system vibration profile, the numerical aperture, spectral smearing and de-coherence, calibration sample and mirror parameters, etc.

Let us consider a sample (e.g. semiconductor sample) measured by the spectral interferometer, to obtain its structural (geometrical and optical properties) parameters (i.e. OCD metrology). As noted above, the measured signal is given by $$|T_k(p,z)|^2 = F_\Omega\{|S_k(p,\Omega)+R_k(\Omega)\cdot\exp(ikz)|^2\} \tag{3}$$

where $R_k(\Omega)$ and $F_\Omega$ are now completely characterized by calibration measurements (either as described above or other suitable technique). Various merit functions (MF) can now be defined which can be optimized in order to obtain the structural parameters p (CD, heights, side wall angles, thickness, material properties, etc.) characterizing the measured sample. An example for such function is given by:

$$M_{Ispect}(p,z) = \tag{4}$$
$$\sum_k |F_\Omega\{|T_k(p,\Omega)+|R_k(\Omega)|\cdot\exp(i\varphi_k)\cdot\exp(ikz)|^2\} - |I(p,z)|^2|$$

where $T_k(p,\Omega)$ is the calculated complex reflectance of the given target sample.

As in any OCD metrology procedure, this merit function MF is used as a measure for 'goodness of fit' between the calculated (theoretical) and measured spectra. Once the application parameters which provide the best fit condition (minimal MF) are found, they are identified as those characterizing the measured sample. The search for the set of application parameters providing the best fit condition, as well as the optimized definition of merit function MF, can be based on the algorithmic approaches used for OCD, as described for example in WO2011/104713, assigned to the assignee of the present application and incorporated herein by reference. Alternatively, as will be described below, the merit function definition can be altered to improve robustness against noise and convergence accuracy.

While for standard OCD, commonly used merit function involve RMS error between calculation and measurement, in the case under consideration here there is additional flexibility in its definition. A possible alternative (more advanced) merit function is the normalized, so called cosine merit function, and is given by:

$$M_{cos}(p,z) = \sum_k |CT_k(p,z) - C_k(z)|, \tag{5}$$

where $$CT_k(p,z) = F_\Omega\{|T_k(p,\Omega)+|R_k(\Omega)|\cdot\exp(i\varphi_k)\cdot\exp(ikz)|^2\} - \tag{6}$$
$$|S_k|^2 - |R_k|^2 / 2|S_k||R_k|$$
$$C_k(z) = |I_k(z)|^2 - |S_k|^2 - |R_k|^2 / 2|S_k||R_k|$$

It is possible to define a general merit function which includes various merits and various measurements at more than one z position:

$$M_{total} = \sum_i \alpha_i M_i(z) \tag{7}$$

Figure 6:
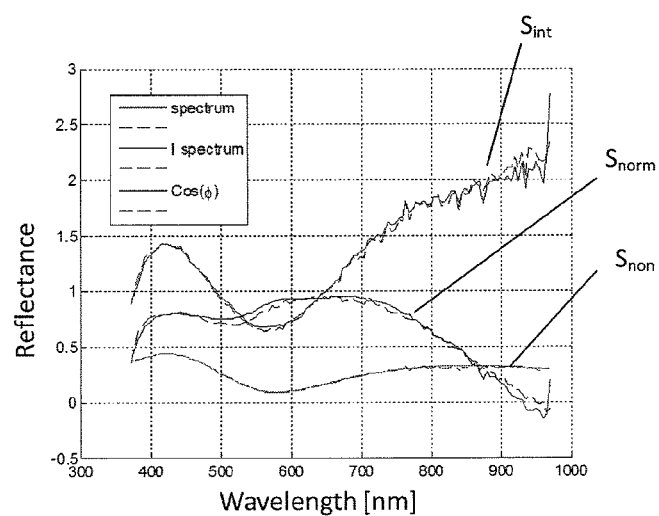
FIG. 6 shows an example for structural parameters obtained by spectral interferometry of the invention.

Reference is made to FIG. 6 which shows an example for structural parameters obtained by spectral interferometry of the invention. This is an example of $SiO_2$ on Si measurements (a blank Silicon wafer with a thin Silicon-Oxide (~2963 Å thickness). Here, the non-interferometric spectrum (curve $S_{non}$) is shown together with the interferometric spectrum (curve $S_{int}$) and the so called Cosine spectrum (curve $S_{norm}$) being the normalized cosine spectrum $C_k(z)$ in equation 6, are shown, where solid and dashed curves correspond to respectively measured and calculated spectra. When using the correct Oxide thickness and z position, the theoretical spectra match the measured ones. It is evident that by optimizing the spectral differences it is possible to obtain the Silicon-Oxide thickness and the z position.

The above mentioned merit functions are only few examples out of many possibilities. It is also possible to use the spectral phase extracted from interferometric measurements or the components of the measured complex field (real and imaginary parts). These entities can be compared to their modeled counterparts and used to find the sample's structural parameters.

Figure 7:
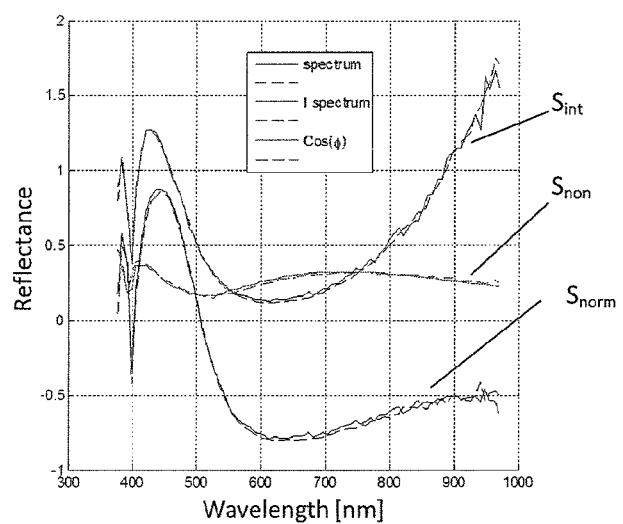
FIG. 7 shows the measured spectra recorded from grating of Silicon-Oxide lines on a Silicon wafer (~1800 Å line width, 1800 Å trench width, 3000 Å line height)

More complex applications, which are customary in the semiconductor industry (including non-blanket samples), can be measured and analyzed as well. Reference is made to FIG. 7 which shows the measured spectra recorded from grating of Silicon-Oxide lines on a Silicon wafer (~1800 Å line width, 1800 Å trench width, 3000 Å line height). In the figure, solid and dashed curves correspond to measured and calculated spectra, and curves $S_{non}$, $S_{int}$, and $S_{norm}$ correspond to, respectively, non-interferometric spectrum, interferometric spectrum and normalized cosine spectrum ($C_k(z)$ in equation 6). Here again, when using the correct structural parameters (Oxide thickness, line spacing, line width and z position), the theoretical spectra match the measured ones.

Instead of using a spectrometer to measure the interference signal for each wavelength separately, it is possible to measure the interference on an achromatic detector (such as CCD camera) and repeat the measurement while scanning the optical distance between the sample and reference (z). Similar approach is used for white light interferometer [Griffiths, P.; de Hasseth, J. A. (18 May 2007). Fourier Transform Infrared Spectrometry (2nd ed.). Wiley-Blackwell. ISBN0-471-19404-2], where spectral information in the IR is obtained by multiple interferometric measurements, varying the reference arm length.

In order to analyze this situation, the optical signals of the sample and reference can be considered accordingly as pulses in the time domain S(t), R(t). A shift in the optical path difference between reference and sample is denoted by a temporal shift τ. Since the detector can be operated to integrate over the total pulse width, such measured signal is given by:

$$P(\tau)=\int |S(t)+R(t-\tau)|^2 dt = \int |S(t)|^2 dt + \int |R(t)|^2 dt + S \otimes R^* + c.c \quad (8)$$

and using Fourier transform:

$$\tilde{P}(\omega)=\int |S(t)|^2 dt + \int |R(t)|^2 dt + \tilde{S}(\omega) \cdot \tilde{R}^*(\omega) + c.c \quad (9)$$

where $\omega = 2\pi c/\lambda$ is the angular frequency.

From the quantity $\tilde{P}(\omega)$ it is possible to obtain the complex sample reflectance $\tilde{S}(\omega)$ since it includes two offset terms ($\int |S(t)|^2 dt, \int |R(t)|^2 dt$) and the reference function $\tilde{R}^*(\omega)$ which can be measured beforehand.

This measurement method actually presents the Fourier conjugate of the above-described spectral interferometry. The spectral axis in the spectral interferometry is replaced here by a spatial axis (z).

Once the complex reflectance $\tilde{S}(\omega)$ is obtained, the above described methods, i.e. Merit function optimization, can be used.

The above described novel approach of the spectral interferometry can be used for accurate spectral phase measurement, following the principle of heterodyne measurement. The principle of heterodyne measurement are generally known and need not be described in details, except to note the following. The heterodyne concept can be considered as a method for encoding the amplitude and phase of a complex-valued signal using only a real-valued signal. An outline for the procedure is as follows: the signal is multiplied by high frequency constant-wave (CW) carrier (as will be described more specifically further below) and the real part is taken to generate the heterodyne signal; the envelope of the heterodyne signal is the amplitude of the original signal; and the shift of the heterodyne signal relative to the carrier is the phase of the original signal.

Figure 8:
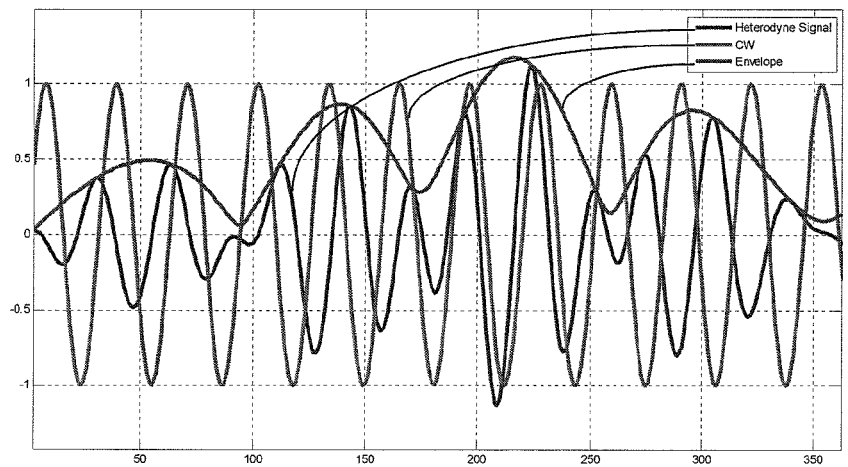
FIG. 8 illustrates a low-frequency signal ('Envelope') multiplied by a CW carrier, providing the heterodyne signal.

FIG. 8 illustrates this concept, showing a low-frequency signal ('Envelope') multiplied by a CW carrier, and providing the heterodyne signal. Both the amplitude and phase of the original signal can be derived from the heterodyne result.

In a white-light interferometer, the spectrum of unbalanced arms acquires a CW component $e^{ik\Delta z}$ with frequency proportional to Δz, being the difference in optical path length between the arms. Here $k=2\pi/\lambda$ denotes the freespace wave number for light of wavelength λ, and for simplicity can be assumes that the reference arm is spectrally neutral. For large enough Δz, this CW component can be used to generate heterodyne signal mixing with the original spectral signal S(k) (complex amplitude and phase) from the sample.

Such large values of Δz can be used to allow the use of heterodyne tools for the signal analysis.

Optical intensity measurement generates a product of signal and carrier $$I(k)=|S(k)+e^{ik\Delta z}|^2=1+|S(k)|^2+2Re\{S(k)e^{-ik\Delta z}\}. \quad (10)$$

This equation (10) is similar to Eq. 1 above, but simplified for clarity (Eq. 1 presents the more comprehensive description).

In equation (10), the last term, $2Re\{S(k)e^{-ik\Delta z}\}$, is the heterodyne signal.

FIGS. 1A-1C show examples of the spectral interferometer enabling spectral heterodyne measurements. A light source 12 used in the interferometer has a sufficient spectral range to cover the spectral region of interest. The interferometer includes a beam-splitter unit 22 which splits input light into a reference arm $L_{ref}$ and a sample (probe) arm $L_p$ that interacts with the sample, and a beam-combiner 26 that combines the output of both arms, after the sample arm interaction with the sample. A control device/mechanism for controlling or generating (a fixed or variable) optical path length difference (OPD) between the arms may be implemented using movable untilted mirror 28 or stationary tilted mirror 128). In the spectral interferometer of the invention shown in FIG. 1A, movement of untilted mirror 28 in the reference arm, or movement of the sample's support 12 is used, if measurement in reflection mode is considered. In the spectral interferometer of the invention shown in FIGS. 1B and 1C, neither mirror nor sample needs to be moved during the measurements, which is achieved by the above-described tilted or defocused configurations. The OPD is to be large enough to generate a CW carrier signal $e^{ik\Delta z}$ with high enough frequency. A spectrometer used for measuring the spectral intensity of the interference signal has suitable spectral resolution for correctly sampling the CW carrier signal whilst retaining sufficient coherence as will be discussed below.

Figure 9:
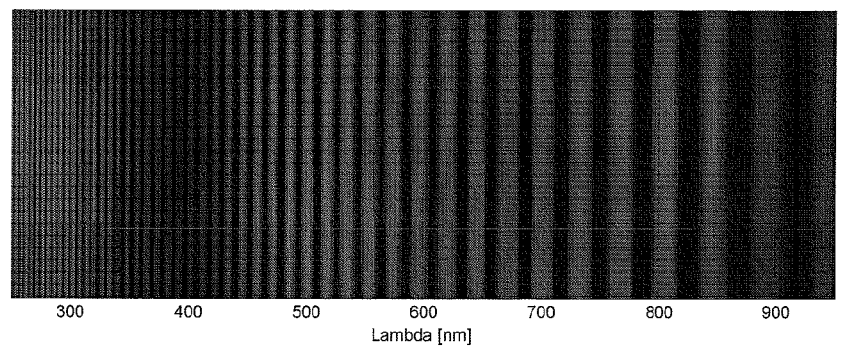
FIG. 9 illustrates the simulation results (calculated heterodyne interference signal) for the interference spectrum from a perfect mirror sample and reference.

FIG. 9 illustrates the simulation results (calculated heterodyne interference signal) for the interference spectrum from a perfect mirror sample and reference. This is the manifestation of the real part of the aforementioned CW carrier signal $e^{ik\Delta z}$, but the horizontal scale is wavelengths (as opposed to wave numbers), and thus the chirped appearance.

The results of the measurements can be interpreted in order to extract the sample's (complex) reflection (both amplitude and phase). As exemplified in FIGS. 1A-1B, the control unit 30 is appropriately configured for processing and analyzing measured data indicative of the spectral interference pattern including two or more spectral interference signatures. This data processing utilizes model based approach. The data processor utility 30D includes fitting module. As will be described below with respect to the heterodyne detection algorithms, direct information on the interference spectrum can be used to infer metrological data on the sample. However, it should be noted that in model-based metrology it is possible to generate models that already produce spectral interference trial measurements to be compared against the actual measurements. The model based approach provides flexibility of which element of the spectra to use. Using the heterodyne detection algorithm of the present invention, provides insight to the required working points for the model-based metrology methods, where meaningful data may be generated by the measurements.

Figure 10:
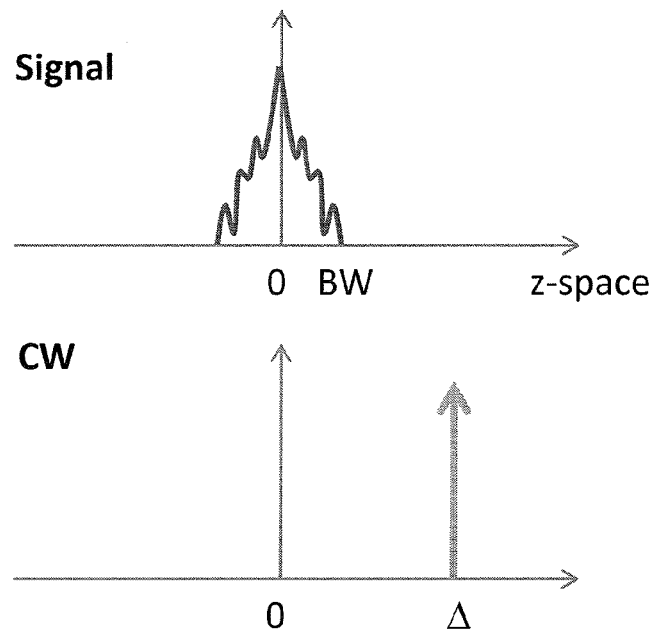
FIG. 10 illustrates the heterodyne scheme, showing bandwidth-limited signal (top) which occupies a region in frequency space ('z' in this case) than the carrier (bottom)

Traditionally, heterodyne detection is based on the spectral properties of the carrier and the bandwidth-limited (BW) signal. More specifically, it is required that they occupy different regions in the frequency spectrum (z-space, which is conjugate to the wavenumber k in the present case). FIG. 10 illustrates the heterodyne scheme, showing bandwidth-limited signal (top) which occupies a region in frequency space ('z' in this case) than the carrier (bottom).

From Eq. 10 above, for a perfect unit reference, the interference signal is:

$$I=1+|S|^2+Se^{-ik\Delta z}+S^*e^{ik\Delta z}. \quad (11)$$

Figure 11:
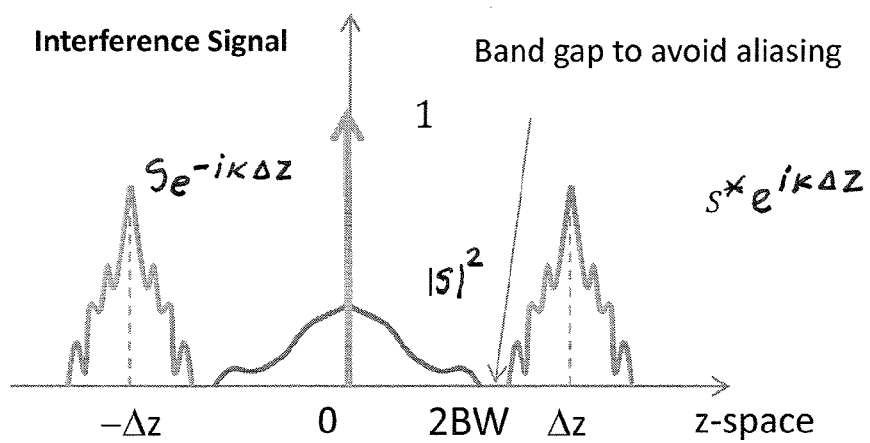
FIG. 11 shows the heterodyne detection in z space.
Figure 12:
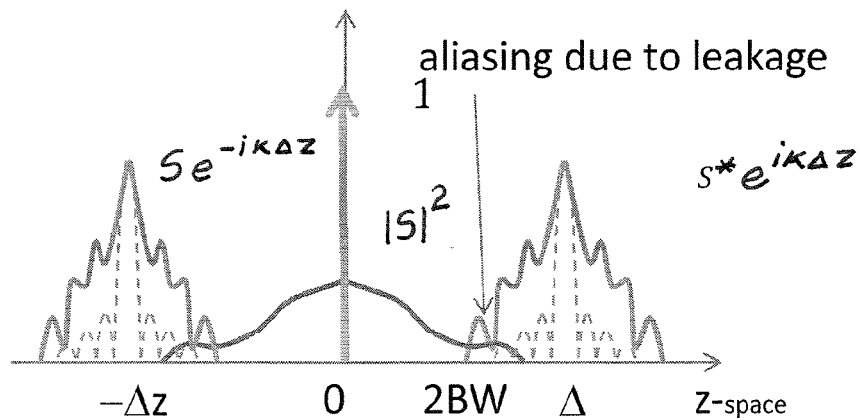
FIG. 12 illustrates practical difficulties with implementing heterodyne methodology.

A frequency space can be used to separate the 4 components in the above sum. This, however, requires the CW frequency to be at least 3 times the signal bandwidth (BW) to avoid aliasing. This is illustrated in FIGS. 11 and 12. FIG. 11 shows the heterodyne detection in z space. The low frequency signal is multiplied by the carrier signal, creating two side lobes. As long as these side lobes have no overlap with low frequency component, heterodyning can be implemented with no aliasing errors. FIG. 12 shows practical difficulties with implementing heterodyne methodology. The discreteness of the measured signal creates an overlap between the signal components in z (frequency) space, leading to aliasing errors.

Then, the third term in eq. 11 is multiplied by the carrier to recover signal $$S = (Se^{-ik\Delta z})e^{ik\Delta z}. \quad (12)$$

However, considering application of this method to spectral measurements as generated by a white-light interferometer, since the interference signal is discretely sampled by the detector, this method is implemented using discrete Fourier transforms. However, discrete Fourier image processing suffers from spectral leakage: any function of k that is non-periodic will leak to adjacent bins. This leads to cross-talk between the 4 components, contaminating the extracted signal. Ensuring that the sample's spectrum and carrier $e^{ik\Delta z}$ are periodic on the measured k-space window is not practical. Windowing the interference signal softens the leakage, but not enough for sensitive metrology applications.

Figure 13:
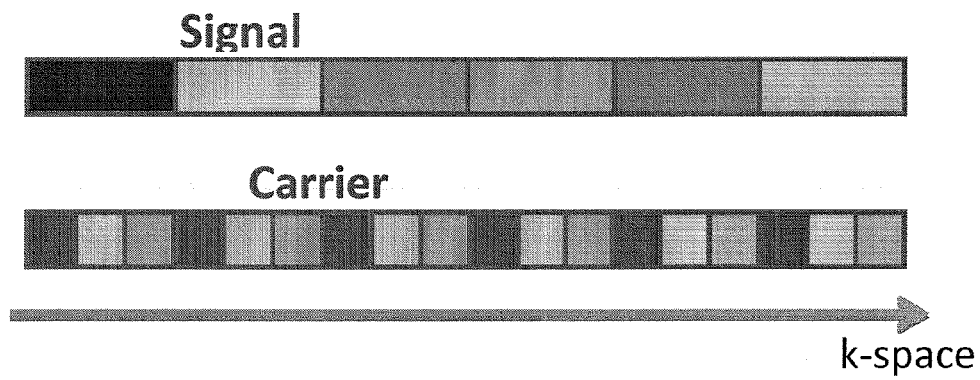
FIG. 13 shows the sampling of the signal of interest by a 3-phase carrier.

In order to overcome the above problems, the invention provides a different approach. It should be noted that in homodyne interferometry at least 3 phase shifts are needed for full recovery of signal. Let us consider the CW carrier as a constantly varying phase shift. Since signal is assumed to vary slowly (3BW≤CW), the carrier samples each signal information "cell" with at least 3 different phases. This is illustrated in FIG. 13 showing the sampling of the signal of interest by a 3-phase carrier.

Assuming the sample signal can be expressed as a sum of a finite number of real-valued basis functions $f_{kn}$, n=1, . . . , N, we have:

$$S_k = \Sigma_n f_{kn}(a_n + ib_n) \quad (13)$$

Possible candidates for suitable basis functions are sincs centered on a suitable k-space sampling grid, sinc-squared on such a grid, or triangle functions (linear 1D finite element shape functions). It should be noted that the sampling grid needs to be adjusted to match the basis function bandwidth, i.e. if the spacing between adjacent functions is too large there will be aliasing problems.

Next, assuming that the sample intensity, $|S_k|^2$, reference intensity, $|R_k|^2$, and interference intensity, $I_k$, have been measured, where k=1, . . . , K, the interference intensity is given by:

$$I_k = |S_k|^2 + |R_k|^2 + \gamma_k(S^*_k R_k e^{+ik\Delta z} + S_k R^*_k e^{-ik\Delta z}) \quad (14)$$

where $\gamma_k \le 1$ is a decoherence term, possibly from z-jitter, finite coherence length, detector noise, integration on pupil or field or both or other degrees of freedom such as polarization, etc.

In order to solve this system of equations, $\gamma_k$ is absorbed into the unknown coefficients, i.e.

$$\gamma_k S_k = \Sigma_n f_{kn}(a_n + ib_n) \quad (15)$$

and then the linear system is solved $$\Sigma_n [|R_k|\cos k\Delta z f_{kn} |R_k|\sin k\Delta z f_{kn}] [{}^{a_n}_{b_n}] = I_k - |S_k|^2 - |R_k|^2 \quad (16)$$

Finally, an estimate for decoherence can be extracted, and the solution is:

$$\gamma_k = \frac{|\Sigma_n f_{kn}(a_n + ib_n)|}{|S_k|} \quad (17)$$

$$S_k = \frac{\Sigma_n f_{kn}(a_n + ib_n)}{\gamma_k} \quad (18)$$

Let us consider degrees of freedom. There are 2N unknown coefficients and K measurements, yielding the requirement K≥2N. This is a reduction compared to the expected 3-fold requirement from the classical heterodyne detection scheme, since the sample intensity $|S_k|^2$ is also measured.

An advantage of the algebraic method is that it accommodates decoherence effects which are hard to control and estimate, and also gives an estimate for their strength. Incorporating the decoherence effects also allows accurate reconstruction of the interference signal in order to obtain a solution residue vs. the actual measurement.

The carrier frequency Δz has to be high enough so that the matrix is well-conditioned and numerically invertible (this is the physical requirement that the phase variation has enough samples of each basis function $f_{kn}$). The last requirement may be traded for several measurements at various lags $z_j$: each basis function $f_{kn}$ is sampled by enough phases due to several $\Delta z_j$. Since solving linear system is fast, unknown parameters can be fit, such as fine-tuning $\Delta z_j$ to minimize the solution residue. This allows fitting on multi-z jump inaccuracies with relatively few numerical resources.

It should be noted that as in any spectral measurement, z-ambiguity in $e^{ik\Delta z}$ means that the spectrum is known only up to a linear phase term. In order to compare the detected signal to a given spectrum, one needs to perform a gauge-fixing procedure, such as (but not limited to) setting the linear phase term to zero, or considering only the second derivative of the phase.

Figure 14:
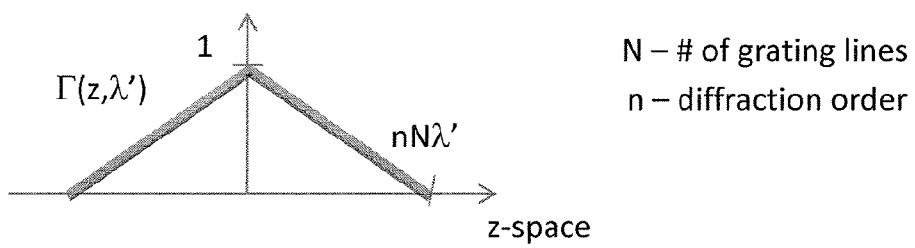
FIG. 14 shows coherence function in z space for a diffraction limited interferometer and a simple grating.

It is thus clear that enough basis functions N is required to correctly describe the assumed spectral signal $S_k = \Sigma_n f_{kn} (a_n + ib_n)$. This, in turn, requires at least K≥2N measurement points, where the carrier oscillates enough for each basis function. This means that Δz has to be large enough so that $e^{ik\Delta z}$ performs one cycle per basis function, and the K sampling points are spaced to correctly sample the interference signal. However, large Δz causes the interference fringe contrast to decrease, as a function of a coherence length of the spectrometer. For a diffraction limited interferometer with a uniform, simple grating, the coherence function has a triangle shape as illustrated in FIG. 14 showing coherence function in z space for a diffraction limited interferometer and a simple grating, where N is the number of grating lines, and n is the diffraction order.

The Fourier transform of the coherence function is the spectral resolution point-spread function (PSF) of the spectrometer:

$$\gamma(\lambda,\lambda') = \sin c^2(2\pi Nn(\lambda-\lambda')/\lambda') \quad (19)$$

Thus, in order to perform heterodyne detection on a spectrum with fine details, a spectrometer needs to have at least twice the spectral resolution required to correctly sample the spectral intensity, and also, since high fringe contrast ensures adequate signal-to-noise ratio (SNR) and may also be required to overcome other possible decoherence causes.

It is possible to bypass the difficulties of interferometric schemes in favor of ultrafast optics techniques. Optical pulses with very short duration (e.g. femtosecond pulses) contain very broad spectral components. The spectral phase of such pulses is generally of interest and as such, various characterization techniques have been studied [Rick Trebino, *Frequency-Resolved Optical Gating: The Measurement of Ultrashort Laser Pulses*. Springer (2002); Mitsuo Takeda et al/. *"Fourier-transform method of fringe-pattern analysis for computer-based topography and interferometry"*. J. Opt. Soc. Am. 72 156 (1982); U.S. Pat. No. 6,611,336]. Most of these techniques make use of non-linear optical interactions to deduce the spectral phase.

In the present case an ultrafast laser pulse is used where all its wavelengths are phase locked (transform limited pulse). The transform limited pulse $$f(t)=\int |F(\omega)|\cdot\exp(i\omega t)d\omega$$

impinging on the sample is transformed to $$s(t)=\int S(\omega)\cdot\exp(i\omega t)d\omega,$$

where $$S(\omega)=|S(\omega)|\cdot\exp(i\varphi_\omega).$$

The new amplitudes $|S(\omega)|$ correspond to the reflectance spectrum of the measured sample. The relative phases $\varphi_\omega$ correspond to the different phase shifts (optical path differences) induced by the sample to each frequency in the pulse. As mentioned, various characterization techniques are able to measure the phase function of the reflected pulse and thus to obtain this crucial applicative information without the need of an interferometer.

Turning back to FIGS. 1B to 1C, illustrating the spectral interferometer of the invention, the sample is illuminated by a white light source through an interferometric objective. The signal is collected and imaged on a spectrograph. The interferometric objective may perform. via e.g. an entrance slit, a 1D imaging of the sample on one axis of its 2D CCD, and unfolds the spectrum of each imaging pixel on the other axis of the CCD.

This setup may have many variants enabling the spectral phase of the reflected field to be extracted, depending on the specific method of extracting the phase, and the ability to assure valid SNR and reduce unwanted system effects.

With the 'standard' interferometry, the phase is extracted by measurements of the sample and reference reflectivity, and of the combined interferometric signal. The use of the spectral interferometric system of the invention provides for obtaining spectrographic data which is richer in spatial information, thus enabling averaging, noise reduction and also measurement of spatial variations of the phase.

Figure 15A:
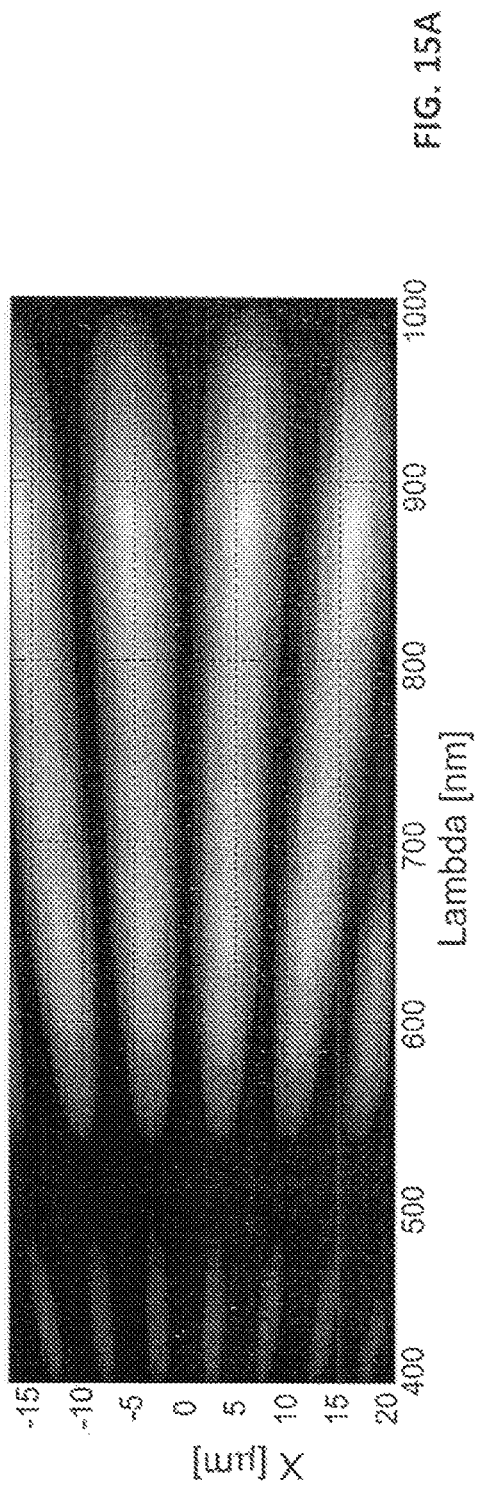
FIGS. 15A and 15B show, respectively, the effect of tilting the sample and\or reference mirror, creating the position-dependent fringes, and the effect of using back focal plane (BFP) imaging, combined with defocusing of the sample/reference mirror.

As described above with reference to FIGS. 1B-1D and 2A, the use of titling the sample and/or the reference mirror, by introducing a tilt to one of the planes or both of them, creates a constant defocus gradient along the imaged axis. This in turn produces linear fringes in the field, caused by the different OPD along the imaged axis. In this connection, reference is made to FIG. 15A showing the effect of tilting the sample and\or reference mirror, creating the position-dependent fringes. This position dependence can be used for accurate extraction of the spectral phase. As the defocus gradient is constant, this will allow better fitting of the signal.

Figure 15B:
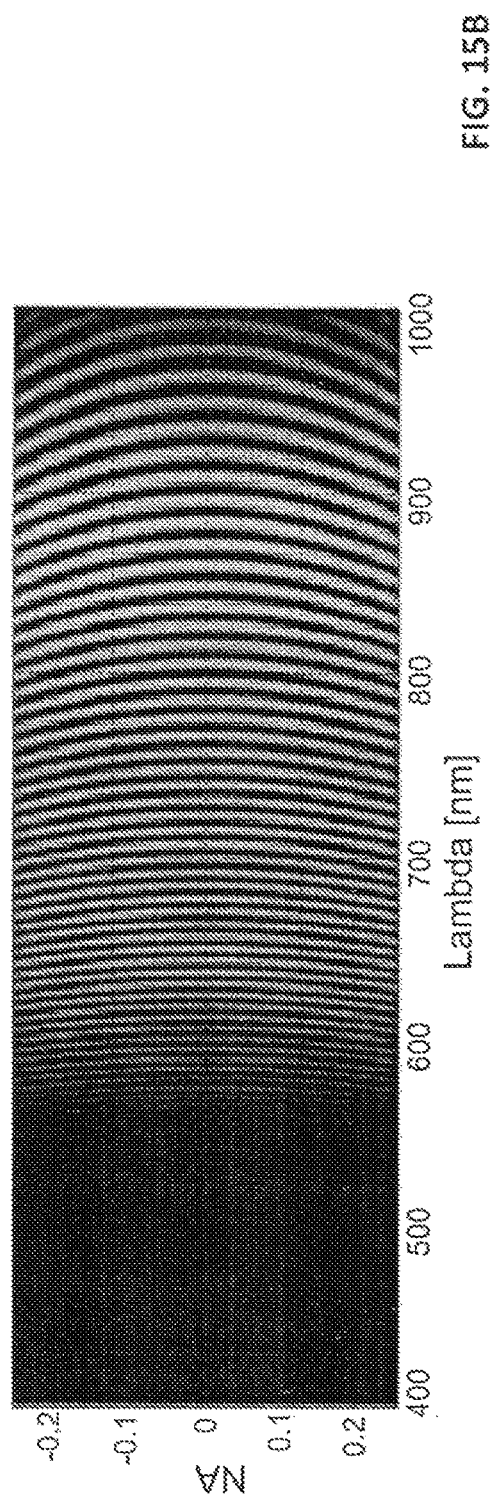

As described above with reference to FIGS. 1B-1D and 2B, alternatively using back focal plane (BFP) imaging, combined with defocusing of the sample/reference mirror, by introducing a defocus to one of the planes or both of them, results in Fresnel fringes in the field, caused by the defocus-dependent phase variation in the NA plane. This is shown in FIG. 15B. By fitting to this fringe pattern, the spectral phase can be extracted with high accuracy. This phase variation has a specific, known, functional dependence Since the defocus is a single parameter, imaging the BFP with the spectrograph improves the ability to extract the spectral phase.

In the above-described methods, the system properties should be considered. For instance, in the BFP with defocusing method, there is an advantage for a larger NA, allowing for defocus sensitivity. Otherwise, large defocus distances must be reached in order for the Fresnel fringes to appear.

Specifically, a system that is designed to measure the angular intensity profile of a target (such as back focal plane imaging or Dome imaging) can be joined with an interferometer to complement the measured data with the phase information. Alternatively, a specially designed wave-front sensor (phase detector) can be used to measure the angular intensity and phase without an interferometer. This option includes various methods of phase and intensity characterization such as "Coherent Point Microscopy" (CPM) described in WO2014/102792) assigned to the assignee of the present application. The CPM technique provides for measuring a light intensity pattern from a sample related to the Fourier transform of the scattering matrix of a sample and thus containing information on both its amplitude and phase. The CPM approach utilizes a combination of an imaging optics in conjunction with coherent light source with so-called "critical illumination", i.e. illumination providing a range of illumination angles onto the sample and coherent interference between different illumination angles. This can, for example, be obtained by directly imaging a point-like source onto the sample under measurements, or alternatively focusing a collimated laser beam on the sample.

The following are some examples of the measured data interpretation.

Many algorithmic approaches can be devised and optimized for interpreting the measured spectral phase. The standard approach to OCD spectral interpretation involves comparing the measured spectrum with a model-based calculation, based on some geometrical description of the measured structure. Many variations and improvements can be used, in the same manner as for other OCD-based methods (library-based, real time regression etc.).

In addition to this approach, it is possible to use a model-less approach, where some features in the measured spectrum are correlated with some parameter characterizing the application. The correlation can be obtained through some physical reasoning or after measuring several samples of known attributes (i.e. semi-empirically).

It is possible to use this metrology approach in combination with any other optical or non-optical metrology method. For example, the acquired information can be used in conjunction with spectral reflectometry, spectral ellipsometry, dome scatterometry, CD-SEM data etc. These complementary datasets can be used to remove correlation between parameters. Alternatively, accurate information from one metrology method (e.g. top-CD from a CD-SEM) can be injected (as a fixed value) into the interpretation process of the spectral interferometry measurement.

As described above, with reference to FIGS. 1B-1D and 2A-2D, the technique of the present invention provides for obtaining required spectral interferometric data for extracting the structure parameters using a single measurement. It should be noted that, if needed, the spectral interferometer of the present invention can provide for a so-called multi-z measurements. Measurements can be obtained for several values of sample height (in direction of the optical axis), or for different positions of the reference mirror, and these measurements are used to extract a cleaner phase measurement. As also described above, z may be used as a fitting parameter, which may be extracted from the measured spectrum.

The measured spectra can be spanned as a linear combination of some basis functional set, thus enabling to rephrase the fitting process in the form of a simple linear problem. The choice of suitable basis functions can improve the fit accuracy, as well as robustness to noise. For the multiple types of basis functions, the approach can be extended, using e.g. higher-order finite-element shape functions. For non-translationally invariant basis functions, the approach can be extended, using e.g. wavelets, polynomials etc.

Information on the temporal coherence of the signal may be included in the fitting process. Accounting for this factor will cause some smearing of the interference spectrum, which could be important (especially if the spectral resolution is not high). The coherence factors can be readily estimated based on the optical parameters of the system. Alternatively, it is possible to deduce the coherence factors from a measurement (one or few), by using the coherence factors as fitting parameters.

Other optical designs of the measurement system can be used, obtained through setups incorporating spectrographs, thus extended the approach of the invention to multi-channel cases.

The measurement system of the invention can use any suitable type of light source, such as lamp, LED, laser, supercontinuum laser, laser driven plasma, others, as well as any illumination type such as Kohler, critical, extended vs. point, etc. Any suitable types of beam splitters/combiners and configurations can be used, such as half-silvered plates, cubes, fiber splitter/combiners, planar lightwave circuit splitter/combiners, as well as polarized beam splitter. Also, separate splitter/combiners can be used (in a Mach-Zehnder configuration) or a single splitter/combiner (in a Michelson configuration). A moving beam splitter can be used to alternate between a standard reflectometry measurement and an interferometric measurement. The detection unit may utilize any spectrometer types and configurations including the option to use a spectrograph to obtain heterodyne spectral measurements in multiple parallel channels (such as, but not limited to, sample cross-section, scattered pupil cross-section), and/or use of a second spectrometer to obtain a measurement of the interferometer combiner's "rejected" channel, and/or use of an additional spectrometer to concurrently obtain pure intensity (non-interferometric) measurements from the sample. The measurement technique of the invention may utilize polarized or unpolarized light, as well as different illumination and collection polarization states during measurements (including various cross-polarization measurements). The optical path length control may be implemented using fixed path length difference, mirrors, retroreflectors, spatial light modulators, liquid crystals, MEMS, etc., as well as control of either the sample path or reference path or both. A MEMS reference mirror can be used to control the OPD and tilts of the interferometer. Also, any suitable scheme of the optical interaction with sample can be used, such as transmission or reflection or double-pass through sample (with a mirror/reflector behind sample), normal and/or oblique illumination and collection angles, oblique at various azimuths, optically resolved or unresolved sample, apodized illumination/collection apertures.

The optical components may also be of any suitable known type, such as objectives of high or low NA, either custom or existing, optimized for laser illumination and/or for broad band, reflective or refractive. Different configurations are possible for the interferometry element, such as Michelson, Mirau, Linnik. It is also possible to reduce noises and non-linearity by extending number of measurements (in different z, or other). Changes could be applied in Fourier plane (such as Phase contrast), or Fourier filtering could be used.

The technique of the invention can be related and combined with other optical techniques, e.g. CPM, in case Bertrand lens is used, of directly obtaining spectral phase in Fourier plane (as described in WO2014/102792 assigned to the assignee of the present application and incorporated herein by reference). Measurements of spectral phase can similarly be integrated into a more comprehensive OCD metrology scheme, implementing other information channels. For example, the spectral phase measurement can accompany an angular phase measurement technique, either as an additional measurement unit, additional measurement head or even a different channel in the same metrology head.

The invention claimed is:

1. A measurement system for use in measuring parameters of a patterned sample, the system comprising: a broadband light source; an optical system configured as an interferometric system; a detection unit; and a control unit; wherein:
    the interferometric system defines illumination and detection channels having a sample arm and a reference arm comprising a reference reflector, and is configured to induce an optical path difference between the sample and reference arms, and to combine output of the sample and reference arms into the detection channel for propagation of a combined light beam formed by a light beam reflected from said reference reflector and a light beam propagating from a sample's support;
    the detection unit comprises a spectral sensor configured and operable to detect the combined light beam, and generate measured data indicative of spectral interference pattern formed by at least two spectral interference signatures corresponding to at least two different values of the optical path difference between the sample and reference arms; and
    said control unit is configured and operable to receive the measured data and apply a model-based processing to the spectral interference pattern for determining one or more parameters of the pattern in the sample.

2. The measurement system of claim 1, wherein said interferometric system comprises polarizers in the illumination and detection channels.

3. The measurement system of claim 2, wherein said interferometric system comprises a driving mechanism associated with either one or both of said reference reflector and the sample's support and configured and operable to controllably move at least one of said reference reflector and the sample's support along an optical axis of the interferometric system, to induce the optical path difference between the sample and reference arms.

4. The measurement system of claim 1, wherein at least one of the sample's support and the reference reflector is oriented with a fixed tilted position with respect to an optical axis of the interferometric system, providing the optical path difference between the sample and reference arms.

5. The measurement system of claim 4, wherein said reflector is located in a plane parallel to and spaced-apart from a focal plane of an objective lens unit of said interferometric system.

6. The measurement system of claim 4, wherein said reflector is configured as a retro-reflector assembly.

7. The measurement system of claim 1, wherein said interferometric system is configured and operable to induce defocusing effect on illuminating light beam propagating along the reference arm towards said reference reflector, providing the optical path difference between the sample and reference arms.

8. The measurement system of claim 1, wherein the light source is configured and operable to produce illumination in the form of ultra short pulses.

9. An optical system for use in measuring parameters of a patterned sample, the optical system being configured as a spectral interferometer comprising an interferometric system and a detection unit comprising a spectral sensor, wherein:
the interferometric system defining illumination and detection channels having a sample arm and a reference arm comprising a reference reflector, and being configured to induce an optical path difference between the sample and reference arms, and to combine output of the sample and reference arms into the detection channel for propagation therethrough of a combined light beam formed by a light beam reflected from said reference reflector and a light beam propagating from a sample, such that said combined light beam is indicative of spectral interference pattern formed by at least two spectral interference signatures corresponding to at least two values of the optical path differences.

10. The optical system of claim 9, comprising polarizers accommodated in the illumination and detection channels and configured to provide cross-polarization scheme.

11. The optical system of claim 10, comprising a mechanism configured and operable to induce the optical path difference between the sample and reference arms.

12. The optical system of claim 11, wherein said mechanism is configured as a driving mechanism to controllably move either one or both of said reflector and the sample's support along an optical axis of the interferometric system.

13. The optical system of claim 10, wherein at least one of the sample's support and the reference reflector is oriented with a fixed tilted position with respect to an optical axis of the interferometric system, thereby inducing the optical path difference between the sample and reference arms.

14. The optical system of claim 10, configured and operable to induce defocusing effect on illuminating light beam propagating along the reference arm towards said reference reflector, providing the optical path difference between the sample and reference arms.

15. The optical system of claim 14, wherein said reflector is located in a plane parallel to and spaced-apart from a focal plane of an objective lens unit of said interferometric system.

16. The optical system of claim 14, wherein said reflector is configured as a retro-reflector assembly.

17. A method for use in Optical Critical Dimension (OCD) measurements of parameters of a patterned sample, the method comprising:
directing broadband light through an interferometric optical system having a sample arm and a reference arm with an optical path difference between the sample and reference arms;
detecting, by a spectral sensor, a combined light beam formed by a light beam reflected from a reflector in the reference arms and a light beam propagating from the sample under measurements, and generating measured data indicative of spectral interference pattern comprising spectral phase information and being formed by at least two spectral interference signatures corresponding to at least two different values of the optical path difference between the sample and reference arms; and
applying a model-based processing to the spectral interference pattern and determining one or more parameters of the pattern in the sample.

18. A measurement system for use in measuring parameters of a patterned sample, the measurement system comprising: a broadband light source; an optical system configured as an interferometric system; a detection unit; and a control unit; wherein
the interferometric system defines illumination and detection channels having a sample arm and a reference arm comprising a reference reflector, and comprising one of the following configurations of optical elements adapted to induce an optical path difference between the sample and reference arms without movement of any of said optical elements: (1) the reference reflector is oriented with a fixed tilted position with respect to an optical axis of the interferometric system; (2) the sample's support is oriented with a fixed tilted position with respect to the optical axis of the interferometric system; (3) the reference reflector is located in a plane parallel to and spaced-apart from a focal plane or a plane conjugate to the focal plane of an objective lens unit of the interferometric system inducing defocusing effect on a reference beam propagating along the reference arm; or (4) the reference reflector is configured as a retro-reflector assembly inducing a field shift to the reference beam;
the detection unit comprises a spectral sensor, which is configured and operable to detect a combined light beam formed by a light beam reflected from said reference reflector and a light beam propagating from a sample's support, and generate measured data indicative of spectral interference pattern formed by at least two spectral interference signatures corresponding to at least two different optical path differences between the sample and reference arms; and
said control unit is configured and operable to receive the measured data and apply a model-based processing to the spectral interference pattern for determining one or more parameters of the pattern in the sample.

19. The system of claim 18, wherein said retro-reflector assembly is configured to create a tilted pupil, defining said configuration inducing the field shift to the reference beam.

* * * * *